United States Patent [19]

Lower

[11] Patent Number: 4,573,458
[45] Date of Patent: Mar. 4, 1986

[54] BONE FIXATION PLATE

[75] Inventor: Jerry L. Lower, Bourbon, Ind.

[73] Assignee: Zimmer, Inc., Warsaw, Ind.

[21] Appl. No.: 698,263

[22] Filed: Feb. 5, 1985

Related U.S. Application Data

[63] Continuation of Ser. No. 408,585, Aug. 17, 1982, abandoned.

[51] Int. Cl.⁴ ............................................. A61F 1/00
[52] U.S. Cl. ............................ 128/92 D; 128/92 B; 128/92 C
[58] Field of Search ............... 128/92 D, 92 B, 92 G, 128/92 BC, 92 C; 3/1.9, 1.91

[56] References Cited

U.S. PATENT DOCUMENTS

| Re. 28,841 | 6/1976 | Allgower et al. | 128/92 D |
|---|---|---|---|
| 1,025,008 | 4/1912 | Miner . | |
| 1,105,105 | 7/1914 | Sherman . | |
| 2,133,859 | 10/1938 | Hawley | 128/92 |
| 2,406,832 | 9/1946 | Hardinge | 128/87 |
| 2,486,303 | 10/1949 | Longfellow | 128/92 |
| 2,501,978 | 3/1950 | Wichman | 128/92 |
| 2,580,821 | 1/1952 | Nicola | 128/92 |
| 2,599,044 | 6/1952 | Brennen | 433/173 |
| 3,463,148 | 8/1969 | Treace | 128/92 |
| 3,593,709 | 7/1971 | Halloran | 128/92 D |
| 3,641,671 | 2/1972 | Roberts | 433/176 |
| 3,955,567 | 5/1976 | Richmond et al. | 128/92 D |
| 4,034,984 | 7/1977 | Crawford | 273/73 D |
| 4,219,015 | 8/1980 | Steinemann | 128/92 D |
| 4,289,124 | 9/1981 | Zickel | 128/92 D |
| 4,364,382 | 12/1982 | Mennen | 128/92 D |
| 4,454,876 | 6/1984 | Mears | 128/92 D |

FOREIGN PATENT DOCUMENTS

| 0052998 | 2/1982 | European Pat. Off. . | |
|---|---|---|---|
| 0048038 | 3/1982 | European Pat. Off. . | |
| 1579575 | 11/1980 | United Kingdom . | |
| 1027162 | 10/1966 | U.S.S.R. | 128/92 D |

OTHER PUBLICATIONS

Robert Mathys Co. Literature—Intervertebral Disc Prosthesis, no date available—1 page.
Burwell, H. N., Internal Fixation in the Treatment of Fractures of the Femoral Shaft, Injury, vol. 2:235–246, Jan. 1971.
Mears, D. C., Materials and Orthopaedic Surgery, Williams & Wilkins 1979, pp. 7,9,305.
Howmedica literature received Feb. 1980 AAOS meeting, Internal Fixation of Acetabular Fractures.
Synthes Catalog p. 279, Bone Plates, date not known.
Zimmer Catalog pages, Bone Plates, PP B46, B84, B85, B118, B119, B120, ©1981.
The Hip Society, The Hip, Chapter 3, The Results of Acetabular Fractures Treated Surgically, pp. 42–85, C. V. Mosby 1979.
Clinical Orthopaedics and Related Research #151, Sep. 1980, Lippincott, Tile, M.; Pennal, G., Pelvic Disruption: Principles of Management, pp. 63–64.
Clinical Orthopaedics and Related Research #151, Sep., 1980, Lippincott, Letournel, E., Acetabulum Fractures: Classification and Management, pp. 102–106.
Muller, Allgower & Willenegger, Fractures of the Acetabulum, 1979, pp. 202–209, Manual of Internal Fixation.
Hownet "Vital. Surgical Appliance (Catalog)", Hownet Corp., New York, N.Y. 1964, p. 16.

Primary Examiner—Richard J. Apley
Assistant Examiner—David J. Isabella
Attorney, Agent, or Firm—Margaret L. Geringer

[57] ABSTRACT

A bone plate for bridging two portions of a broken bone which can be formed to fit and retain many irregular surfaces and yet retain optimum strength. The bone plate is particularly adaptable for fracture in the pelvic and acetabular area, although the plate is also adaptable for other bone areas. The bone plate is comprised of a solid elongated rod portion and a plurality of screw retaining areas extending from the rod portion and spaced apart from each other along the rod portion, forming rod segments between the protruding screw retaining areas. The plates may be of predetermined lengths and curves to fit specific bones and contours or the plates may be supplied as straight stock that may be cut and contoured according to specific needs.

23 Claims, 15 Drawing Figures

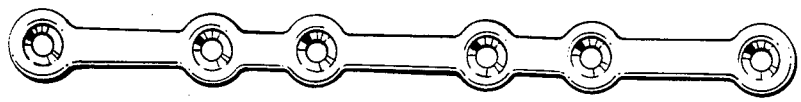
FIG. 1A.
PRIOR ART
FIG. 1B.
PRIOR ART
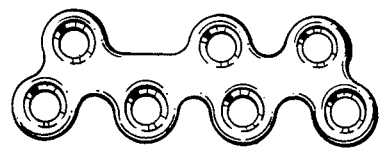
FIG. 2A.
PRIOR ART
FIG. 2B.
PRIOR ART
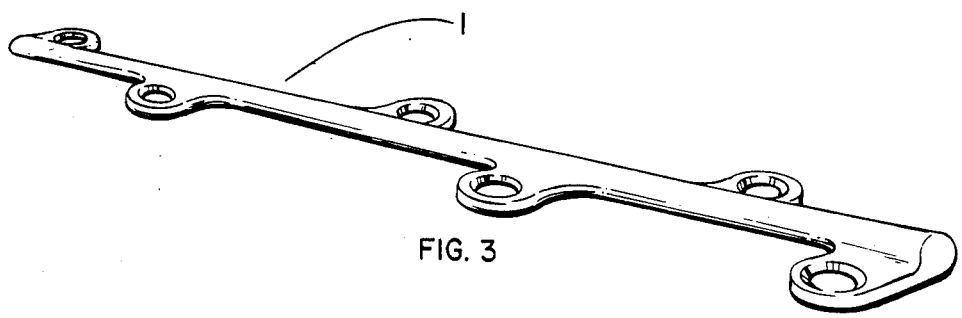
FIG. 3

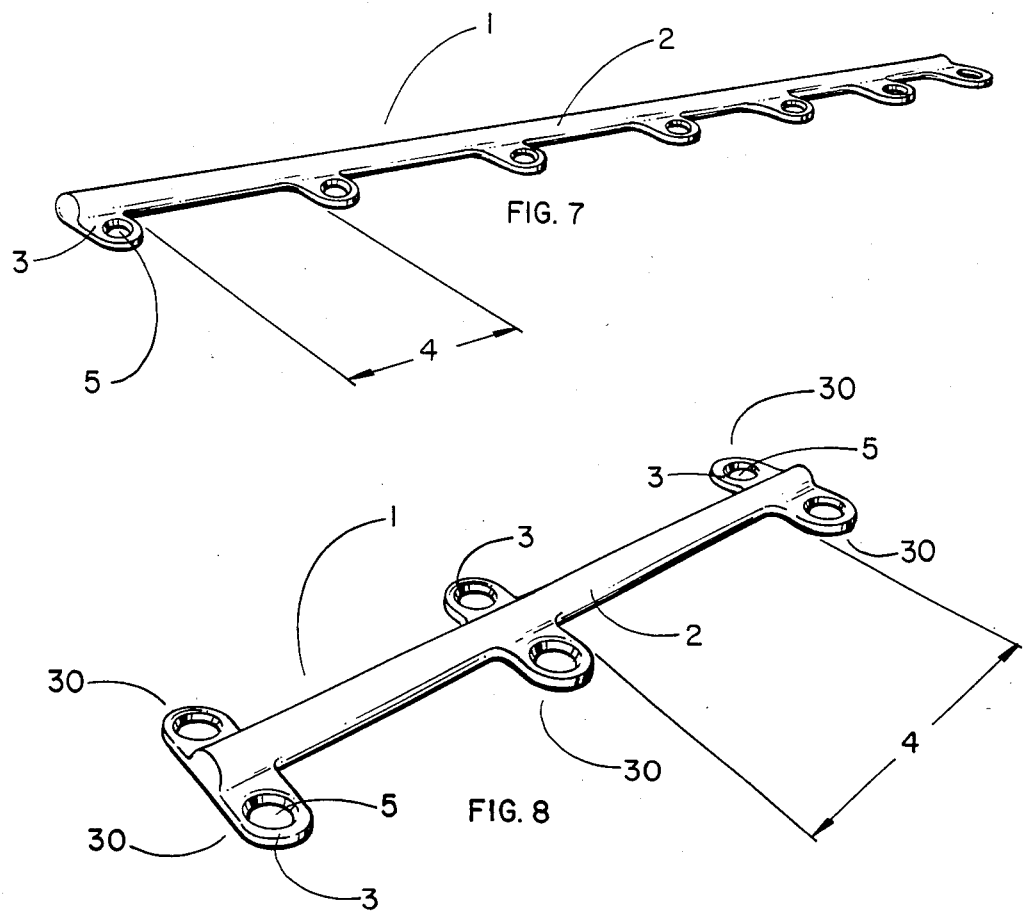

BONE FIXATION PLATE

BACKGROUND OF THE INVENTION

This application is a continuation of application Ser. No. 408,585, filed Aug. 17, 1982, now abandoned.

The present invention generally relates to bone plates for the internal fixation of fractures.

A wide variety of internal bone plates are known in the art for fixation of bone fractures. Bone plates are generally affixed to the bone by means of some type of bone screw. The surface of the plate that bears against the bone is generally flat or slightly curved. Various types of screw holes or slots are known in the art. Some types of holes are adapted to apply a pressure to hold the bone parts in tight engagement. Such a plate is described in U.S. Pat. No. Re. 28,841 to Allgower, et al. In addition, bone plates may come in a wide assortment of lengths and having a varying number of screw holes.

Although, available bone plate styles may vary in thickness, which is the dimension parallel to central axis of the screw holes, they generally have a flat cross-section since the width of the plate is substantially larger than the thickness. In many cases this flat or rectangular cross-sectional shape has a slight curvature in order to conform better to the bone surface.

Many plates are formed as straight elongated plates. Others are manufactured with a pre-formed contour to fit certain bone areas. Also, plates may have more than one elongated section, such as a plate having a "Y" shape. Additionally, certain plates are manufactured from straight stock with the intention that they may be bent or contoured to conform to a certain contour or curvature to adapt to a specific individual need. This contouring, of course, must be done with extreme care as bending of plates can weaken the plate, and increase the risk of breakage. It is usually accomplished by means of a bending press and/or a bending iron. Care must be taken during contouring to avoid twisting or bending a plate at a plate hole. The plate also should not be bent to acute angles or reverse bent, i.e.—bent in one direction and then bent back again.

The breakage point of the known types of bone plates tends to occur at one of the screwholes, since the cross-sectional area which is reduced at these locations influences the strength of the plate in tensile stress. The screw holes of known bone plate designs are positioned within the main body of the bone plate. Therefore, the screw holes act as stress concentrators which weaken the plate.

Also, of importance is a bone plate's bending stress. Additionally, as described in U.S. Pat. No. 4,219,015 to Steinmann, the bone plate should, preferably, have a bending resistance matched to the bone to be fixed. If the plate is very flexible, then the region of the fracture is not sufficiently stabilized and bone resorption in the fracture gap results due to movement. On the other hand, if the plate is very stiff, then the plate takes up all loading forces. The functional loading of the bone is then absent and this may lead to general decay of the bone. Between the two extremes lies an optimum stiffness which is a function of the shape of the plate and of the specific elasticity of the material.

Fractures of the acetabulum and pelvic area are often not uniform because the size and shape of these bones vary significantly from patient to patient, consequently, it is particularly difficult to adapt one plate to the contour of these variably shaped bones. One such plate which is presently known, and is presently being utilized for fracture fixation of the acetabular bone area is the Sherman plate. A Sherman-type plate is sold by Zimmer, Inc. as Product Numbers 125-01/14, and is illustrated in FIGS. 1A and 1B. The Sherman plate is relatively thin. It may be manufactured with various pre-formed curvatures along its length, or it may be manufactured as a straight plate. The straight plate may be contoured to conform to the shape of the acetabulum or pelvis, as previously discussed, with a bending press. In either case, particular care must be taken with this thin plate not to cause a fracture during the bending.

Another prior art plate is illustrated in FIGS. 2A and 2B. This plate is called a Small Fragment Plate and is sold by Zimmer as Product Number 2456-00-07. This plate is generally for use in multiple fractures of small bones. As can be seen in FIG. 2B, the plate is slightly concave and has a relatively thin cross-section.

Another plate which is similar in shape to the Small Fragment Plate is the Serpentine Plate sold by the London Splint Co. This plate is illustrated on page 243 of an article which appeared in INJURY Vol. 2, No. 3, pp 235–246, January 1971. Like the Small Fragment Plate, the Serpentine Plate is a broad plate having alternately positioned screw holes. This plate also has a relatively thin cross-section which is slightly concave. The Serpentine Plate is a strong plate which is suitable for the fixation of fractures of large bones, such as the femur. It is also a rigid plate and therefore is generally not suitable for molding or shaping to a certain bone contour.

The majority of known plates have a substantially rectangular cross-section wherein one of the two wider longitudinal surfaces forms the bearing surface intended to bear on the bone. These plates have either a longitudinal surface that is flat or has a slight concavity, so as to permit conformation to the outer surface of the bone.

OBJECTS OF THE INVENTION

A principal object of this invention is to provide a bone plate which is capable of being easily bent or contoured while minimizing damage to the rod's strength.

Another object of the invention is to provide a bone plate which has a cross-section which enables the plate to be easily bent or twisted to fit an irregular contour.

A further object of this invention is to provide a bone plate which has minimal or reduced stress concentrations.

A still further object of the invention is to provide a bone plate which may be conveniently adapted for use for acetabular and pelvic fractures.

SUMMARY OF THE INVENTION

The present invention accomplishes all of the above objects of invention. The present invention provides a bone plate which includes a solid elongated rod and a plurality of integral screw retaining areas extending from the rod. The screw retaining areas are spaced apart from each other along the rod defining uninterrupted rod segments between the screw retaining areas. The screw retaining areas include a protruding tab portion and a suitable screw retaining opening or hole disposed within the tab portion.

The rods may be of varying lengths and may include various numbers of screw retaining tabs, although it is essential that there be at least two tab portions. The screw holes may be of any suitable kind of hole for retaining a bone screw. For example, they may be the type of screw hole which is designed to produce compression of bone fragments. The bone plate may be made of any suitable implantable material. Examples of suitable materials are titanium, stainless steel, or cobalt-chrome, although it is understood that the material is not limited to these examples.

The screw-retaining tabs may be positioned in pairs opposite each other, or they may alternate from one side to the other side or they may all be placed on one side of the rod. Other suitable arrangements of the protruding tabs may be used.

The bone plate may be manufactured with predetermined lengths and curves to fit specific bones and contours, or the bone plate may be supplied as straight stock that may be cut to the desired length and formed to a particular contour, as needed.

As mentioned, the areas of the elongated rod between the tabs are called rod segments. The rod segments between the tabs have a lower resistance to bending than does the portion of the rod having the tab portion extending therefrom. The minimizing of stress concentration between the tabs insures that most of the bending will occur along the rod segment. Thus, the risk of breakage is reduced with the present plate design because bending occurs at the rod segment which does not include a screw hole portion. This structural arrangement is distinguished from the presently available bone plates wherein breakage typically occurs at the screw holes, because the cross-section of the plate and, consequently the strength of the plate, is reduced there.

During contouring maximum bending stress occurs at the surface of the rod. Ideally, the rod should be circular in cross-section, since a circular rod has a cross-section in which the outside surface of the rod is approximately equal distance about the center axis of the elongated rod. Therefore, the rod can be more easily bent or twisted in any direction while minimizing damage to the rod's strength. However, because of the need to provide more adequate bone surface contact, this ideal may be modified so that the circular shape is blended into a flattened under-side portion in the same plane as the underneath portion of the tabs. This flattened underneath portion is the surface which bears against the bone. This circular and modified circular shape allows for substantially equivalent bending stresses in any direction of unit deflection. Thus, the required bending stresses are minimized in all directions to contour the rod into an irregular shape. It is noted that other cross-sectional shapes have been utilized in the art, but they do not approach the ideal of substantially equivalent bending stresses in any direction of unit deflection.

BRIEF DESCRIPTION OF THE DRAWINGS

These features and objects of the invention, as well as others, will become apparent to those skilled in the art by referring to the accompanying drawings in which:

FIG. 1A is a top view of a Sherman-type Plate which is a prior art bone plate;

FIG. 1B is an end view of the Sherman-type Plate of FIG. 1A;

FIG. 2A is a top view of a Small Fragment Plate which is a prior art bone plate;

FIG. 2B is an end view of the Small Fragment Plate of FIG. 2A;

FIG. 3 is a prespective view of a particular embodiment of the bone plate of the present invention;

FIG. 7 is a perspective view of an alternate embodiment of the bone plate of the present invention;

FIG. 8 is a perspective view of a further alternate embodiment of the bone plate of the present invention;

DETAILED DESCRIPTION OF THE INVENTION

Figures 4A, 4B:
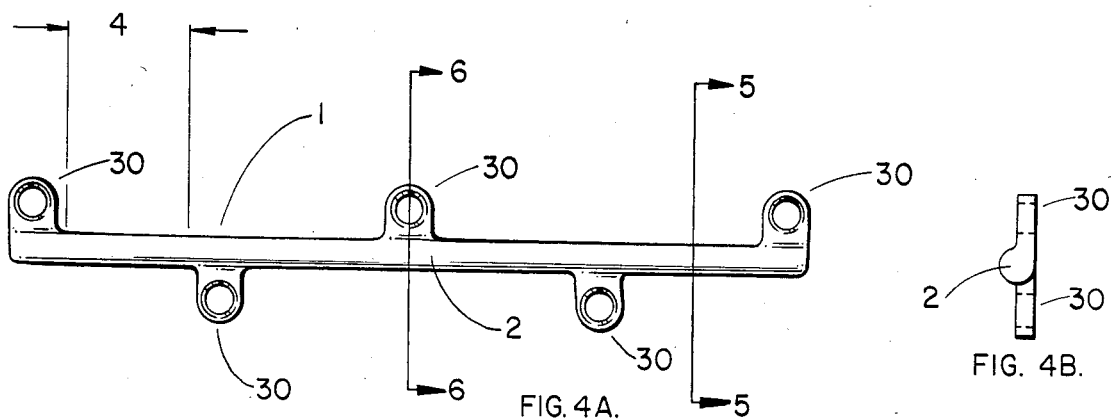
FIG. 4A is a top view of the bone plate of FIG. 3.
FIG. 4B is an end view of the bone plate of FIG. 4A.

FIGS. 3-8 illustrate the implantable bone fixation plate according to this invention. Referring now to FIGS. 3-6 which illustrate a particular embodiment of the present invention, the bone plate 1 includes a solid elongated rod 2 as the main body portion and a plurality of integral screw retaining areas 30 which are attached to and protrude from the rod 2. The screw retaining areas 30 include a protruding tab portion or tab 3 and a suitable screw retaining opening or hole 5 disposed within the tab portion 3. The tabs 3 are spaced apart from each other along the length of the rod 2 so as to define uninterrupted rod segments 4 therebetween. These rod segments 4 preferably have a constant cross-section throughout their lengths as shown in FIGS. 4A, 7 and 8. The tabs 3 are preferably equally spaced apart. The rod 2 or main body portion is continuous and does not include any bone screw openings.

Figure 6:
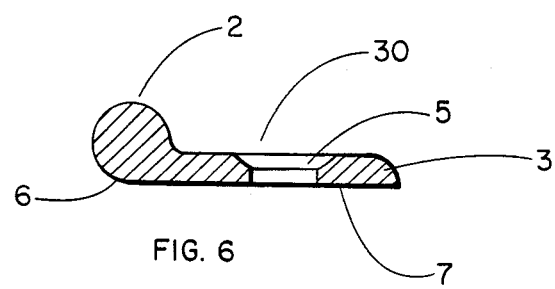
FIG. 6 is an enlarged cross-sectional view of the bone plate of FIG. 4A taken along lines 6—6 and in which the cross-section of the rod segment may be as shown in either FIGS. 5A, B or D.
Figure 9:
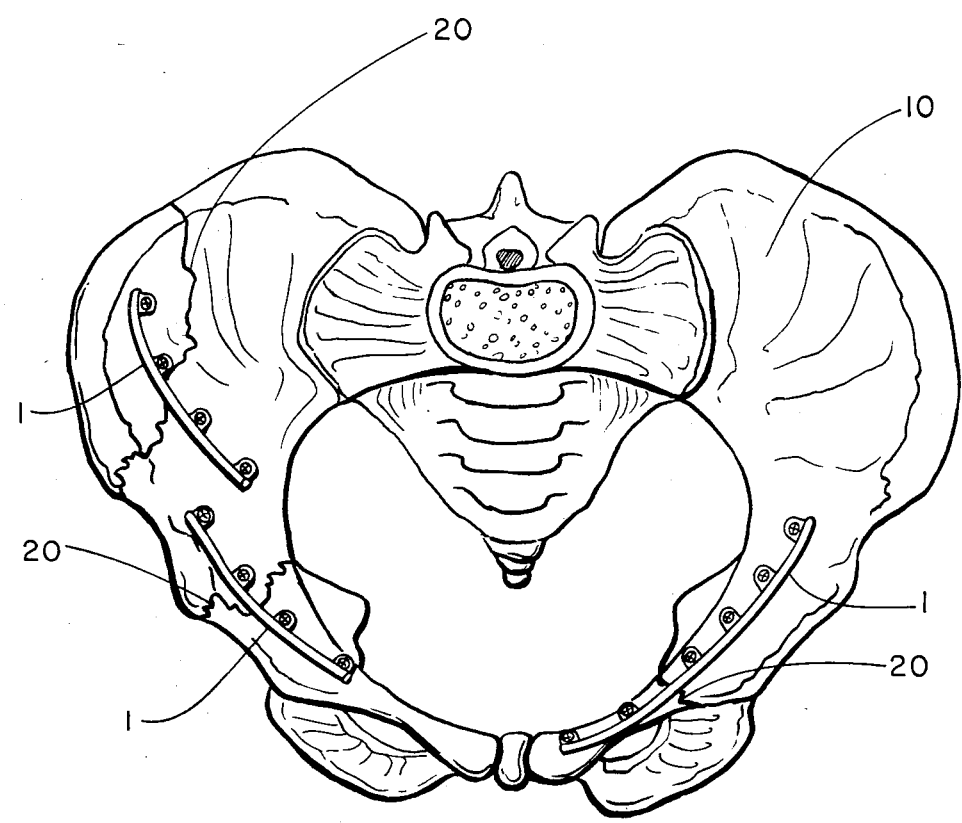
FIG. 9 illustrates the human pelvic bone structure, and further illustrates a number of bone plates of the present invention secured to the bone across various fracture sites.

A cross-section of the rod 2 with an integrally attached screw retaining area 30 is illustrated in FIG. 6. The rod portion 2 has the thinner and substantially flat protruding tab 3 extending from it. The bottom surface 7 of the tabs 3 is substantially flat, and extends in substantially the same plane as the bottom surface 6 of the rod 2. The tabs 3 blend gradually into the rod portion 2 to minimize the stress concentration junctions between the tabs 3 and the rod 2.

In the bone plate 1 of FIGS. 3-6, the tabs 3 are alternately spaced on opposite sides along the length of the rod. This plate 1 includes five tabs 3 alternately positioned. It is understood that the plates may be manufactured in various lengths with a varying number of tabs.

FIGS. 7 and 8 illustrate alternate embodiments to the invention. FIG. 7 illustrates a bone plate 1, in which the tabs 3 are all aligned on the same side of the plate 1. This is referred to as parallel positioning of the tabs. With both the alternate tab positioning (FIG. 1) and the parallel positioning (FIG. 7) at least two tab portions 3 are required, although preferably more than two tab portions 3 would be utilized. Clearly, combinations of parallel and alternate positioning within the same bone plate is within the scope of the invention.

FIG. 8 illustrates a bone plate 1 in which the tabs 3 are positioned in pairs with one half of each pair positioned on one side of the rod 2 and the other half of each pair positioned directly opposite on the other side of the rod 2 from its corresponding half. This arrangement is referred to as opposite positioning. At least two pairs of tabs are required with opposite positioning.

It often is preferable to include at least four or more screw retaining areas 30 in order to prevent moment induced fracture separation. These are cases where a single screw placed on each side of the fracture would be unable to prevent rotational motion of the rod, hence the fracture might separate if less than four screws were used to fix the plate. It is also readily apparent to those skilled in the art, that there are possible fracture configurations that exist where only two screws, one each side of the fracture, would be necessary to prevent fracture separation.

The plate may be of a predetermined length with a predetermined number of tabs, or it may be cut to the desired length with an appropriate rod cutting tool.

The plates 1 may be manufactured with pre-formed contours or they may be manufactured from straight stock. The plates 1 may be contoured or bent in any direction to fit an irregular contour by a suitable bending instrument. For example, a suitable tool can be used for grasping or applying an appropriate force about the rod. The bending can be applied as needed along the length of the rod in order to achieve the desired contour. Care should be taken not to reverse bend the rod or to bend the rod to acute angles. The rod segments 4 between the tabs 3 have a lower resistance to bending than the portion of the plate 1 having the tab sections protruding therefrom, thus the bending occurs at the rod segment 4.

As previously mentioned, the breakage point of other known types of plates usually occurs at one of the screwholes, since the strength of the plate is generally reduced at these locations. When contouring these other known types of plates, care must be taken not to bend the plate at a screwhole because this would increase the risk of breakage. However, with the plate 1 of the present invention, bending will occur at the rod segment 4. It should be noted that with the plate 1 of the present invention, if breakage should occur at a hole 5 or tab 3, the continuity of the rod 2 would not be lost since the holes 5 are not in the main body of rod portion 2 of the plate 1. The plates 1 of the present invention allow bending or twisting of the rod 2 while minimizing damage to the rod's strength. Also, maximum bending stresses occur at the surface which has minimal or reduced stress concentrations.

Most other known types of plates utilize a substantially rectangular cross-section or a slightly curved relatively thin flat cross-section. Ideally the cross-section of the rod 2 of the present invention would be circular. A circular cross-section has an outer surface which is closer to the center lengthwise axis in comparison to any other plate. A circular section's strength in bending will be compared below to a rectangular section by analyzing the section modulus. The section modulus for a circular cross-section is $(\pi D^3/32)$ where (D) is the diameter of the rod 2 in (mm). The section modulus of the rectangular section is $(BH^2/6)$ where (B) is the base width and H is the height (thickness) in (mm). Unlike a circular cross-section, the axis in which the section modulus is taken about in a rectangular section is important. For example, a plate having a cross-section of 4.5×2 mm has a section modulus of 3 mm$^3$ about the longer axis, and a modulus of 6.8 mm$^3$, about the short axis. A 4 mm diameter rod has a section modulus of 6.3 mm$^3$. The cross-section area of a rectangular 4.5×2 mm plate is 9 mm$^2$, and the cross-section area of a 4 mm diameter rod has an area of 12.56 mm$^2$. Cross-sectional area is directly proportional to the tensile load a design, assuming like materials, neglecting stress risers and neglecting material removed for holes.

An exact comparison between the strength of a rectangular cross-section versus the round cross-section is complicated by stress concentrating factors, different materials used, and method of bending the plates. Both rod and plate design will be plagued with the problems of stress risers due to scratches on the surface of the plate from manufacturing, shipping, and bending. The stress across a screw hole on a flat plate, will be multiplied by a concentration factor of $(Kt \geq 1.9)$. This is explained in further detail in *Stress Concentration Factors* by R. E. Peterson. The rod design of the present invention does not have this additional stress concentration problem because the hole is external to the stressed region. Having minimized the stress risers, the rod 2 of the present invention can compare to a higher strength plate of the type having holes in the main body.

Figures 5A, 5B:
FIG. 5A is an enlarged cross-sectional view of the bone plate of FIG. 4A taken along lines 5—5.
FIG. 5B is an alternate cross-sectional view of the bone plate of FIG. 4A taken along lines 5—5.

The circular cross-section illustrated in FIG. 5B is an ideal case. Other cross-sections with relative closeness of the outer surface of the rod 2 to their center longitudinal axis, such as a square or hexagon or a circle with the extreme portion of one end of the circle being flattened out, will perform similar to the circular cross-section. A determining factor to the cross-sectional configuration is the manufacturing process. The advantages of manufacturing and rod design must be optimized. The advantage of utilizing a rod cross-section in which the outside surface of the rod is of approximately equal distance about the center axis of the elongated rod is that the rod can be more easily bent or twisted in any direction while minimizing damage to the rod's strength. Whereas, with a thin rectangular plate, the rod will bend more easily across the thinner thickness than across the wider dimension and hence is more restricted in its ability to be contoured.

It is preferred that the cross-section of the solid rod 2 of the plate 1, be constant throughout. FIGS. 5A–D illustrate various cross-sections for the rod segments 4 which would be suitable and would generally allow bending and twisting in any direction while minimizing damage to the rod's strength. FIG. 5B illustrates the ideal case of the circular cross-section. However, a substantially circular cross-section in which the circular shape blends into a substantially flattened bottom surface 6 would be more practically suitable, since the substantially flattened surface 6 would be the surface which contacts and bears against the bone surface. Therefore, a substantially flat bottom surface 6 on the rod 2 would provide better contact between the bone plate 1 and the bone to which the plate 1 is attached. Preferably, in the example of FIG. 5A, where the circular cross-section is blended into a flat bottom surface 6, at least 60% of the ideal circular shape still remains before blending into the flat bottom surface 6. The bottom surface 6 of the rod 2 could also have a slight concavity to it, if desirable.

Figures 5C, 5D:
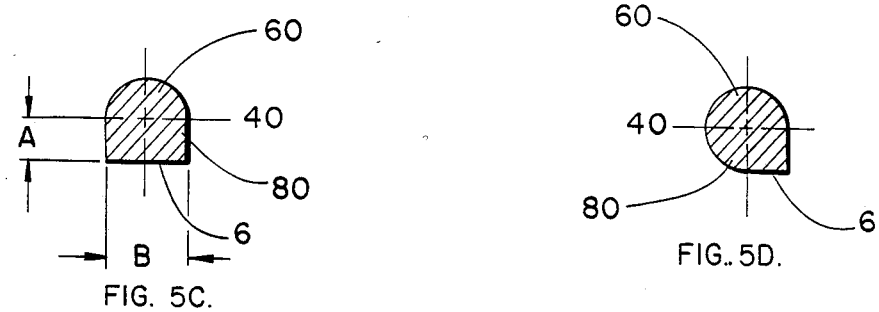
FIG. 5C is another alternate cross-sectional view of the bone plate of FIG. 4A taken along lines 5—5.
FIG. 5D is a further alternate cross-sectional view of the bone plate of FIG. 4A taken along lines 5—5.

FIGS. 5C and D show other alternate cross-sections. In both FIGS. 5C and D, the cross-section has an upper portion 60, above line 40, which is semi-circular, and a lower portion 80 below line 40, which is integrally connected to the upper portion 60. In FIG. 5C, the lower portion is rectangular, such that the "A" dimension of the rectangle is equal to the radius of the semi-circular portion and the "B" dimension is equal to the diameter of the semi-circular portion. FIG. 5D is similar to FIG. 5C except that more of the circular cross-section continues into the lower portion 80, as shown.

In each of the examples of FIGS. 5A, C and D, the flattened bottom surface 7 of the screw retaining areas 30 (shown in FIG. 6) extends in the same plane from the substantially flat bottom surface 6 of the lower portion 80 of the rod 2. In the example of the ideal circular cross-section of FIG. 5B, the flat bottom surface 7 of the screw retaining areas 30 (shown in FIG. 6) would extend tangent from the bottom of the circular cross-section.

It is essential that the rod segments 4 be long enough to enable the desired bending. It is preferable that the minimum length of the rod segment 4 be approximately equal to the diameter of the rod segment 4. If the rod segment 4 does not have a circular diameter, then diameter is defined to the width (W) of the rod segment 4. In addition, it is also preferred that the rod segments 4 be at least 3 mm and no greater than 25 mm in length. It is also preferred that the rod 2 have a diameter of at least 3 mm and no greater than 6 mm. The thickness of the tabs should preferably be at least 1 mm thick and no greater than 4 mm thick. It is understood that the size of the tabs 3 may vary in order to accommodate various size and shape screw holes. One particularly suitable combination is to use a 3.5 mm screw hole in conjunction with a 4 mm diameter rod 2.

The rod 2 design of the present invention preferably has a cross-sectional shape in which the outer surface of the rod 2 is of approximately equal distance about the center axis of the rod 2. The advantages of this, in conjunction with having the solid lengths of rod segment 4 between the tabs 3, is that the rod 2 can be easily contoured while minimizing damage to the rod's strength. Since the bending will occur at the rod segment, since these segments have a lower resistance to bending, there is less risk of the rod eventually fracturing. Bone plate breakage tends to occur at one of the screwholes. Therefore, with the present invention, this risk due to the contouring the plate is minimized. Also, if breakage should occur at a hole 5 or tab 3, the continuity of the rod 2 is not lost, as with other plates. Having a cross-section in which the outside surface is approximately equal distance about the center axis of the elongated rod enables the rod to be bent or twisted in any direction since the bending resistance would be approximately equal in any direction. While the circular cross-section would be ideal, other cross-sections with relative closeness of the outer rod surface to the center axis of the rod (i.e., hexagon, circle with a flattened surface, etc.) will perform in a similar manner.

FIG. 11 illustrates a number of plates 1 of the present invention secured to the pelvic bone structure 10 positioned across various fractures 20. It can readily be seen that the bone plate 1 of the present invention is particularly suited for pelvic and acetabular fractures, although it is also understood that the invention is not limited to this use, but also may be adapted for use on fracture fixation of any suitable bone.

The invention described here is an implantable bone fixation plate. While this invention has been described and exemplified in terms of various particularly advantageous embodiments, those skilled in the art can appreciate that modifications can be made without departing from the spirit and scope of this invention.

I claim:

1. An implantable bone plate comprising:
    (a) a solid, elongated rod, void of any holes throughout its length; and
    (b) a plurality of integral tab members protruding laterally from said solid rod, said tab members having an aperture therein for receiving a bone screw or the like, and wherein said tab members have a thickness less than the thickness of the rod and wherein said rod includes a bottom bearing surface and wherein said tab members have a bottom surface extending in substantially the same plane as the bearing surface of the rod.

2. An implantable bone plate as described in claim 1 wherein said rod has a constant cross-sectional configuration throughout.

3. An implantable bone plate as described in claim 1 wherein said protruding tab members are spaced apart along the length of the rod and define rod segments therebetween.

4. An implantable bone plate as described in claim 3 wherein said rod segments have a constant cross-sectional configuration throughout.

5. An implantable bone plate as described in claim 4 wherein the minimum length of each rod segment is substantially equal to the diameter of the rod segment.

6. An implantable bone plate as described in claim 2 wherein said cross-sectional configuration of the rod is substantially circular.

7. An implantable bone plate as described in claim 2 wherein said rod has a semi-cylindrical upper portion and a lower portion integrally connected to said upper portion.

8. An implantable bone plate as described in claim 7 wherein the thickness of the rod is less than or equal to the diameter of the cylindrical upper portion.

9. An implantable bone plate as described in claim 7 wherein said bearing surface is substantially flat.

10. An implantable bone plate as described in claim 1 wherein the elongated rod includes a cross-section in which the outer surface of the rod is of approximately equal distance about the center axis of the elongated rod.

11. An implantable elongated bone plate as described in claim 1 wherein said protruding tab members are alternately spaced on opposite sides of the rod.

12. An implantable elongated bone plate as described in claim 1 wherein said protruding tab members are spaced in a parallel relationship along one side of the elongated rod.

13. An implantable elongated bone plate as described in claim 1 wherein said plurality of protruding tab members are spaced in pairs, with each member of a pair positioned on an opposite side of the rod from the other member of said pair.

14. An implantable bone plate comprising:
    (a) a solid, elongated rod, void of any holes throughout its length; and
    (b) a plurality of integral tab members protruding laterally from said solid rod, said tab members having an aperture therein for receiving a bone screw of the like, and wherein said tab members have a thickness less than the thickness of the rod, and wherein said rod has a constant cross-sectional configuration throughout and said cross-sectional configuration is substantially circular except along the bottom surface of the rod which flattens substantially out to a planar portion perpendicular to the thickness of the rod.

15. An implantable elongated bone plate as described in claim 14 wherein the screw retaining areas have a substantially flat bottom surface extending in substantially the same plane as the bottom surface of the elongated rod.

16. An implantable bone plate comprising:
(a) a solid, elongated rod, void of any holes throughout its length; and
(b) a plurality of integral screw retaining areas protruding laterally from said solid rod, said rod having a constant cross-sectional configuration throughout, said cross-sectional configuration being substantially circular except along the bottom surface of the rod which flattens substantially out to a planar portion perpendicular to the thickness of the rod, wherein at least 60% of the ideal circular cross-sectional configuration still remains before blending into the flat bottom surface.

17. An implantable elongated bone plate as described in claim 3 wherein said rod segments are at least 3 mm in length and no greater than 25 mm in length.

18. An implantable elongated bone plate as described in claim 3 wherein the rod has a diameter of at least 3 mm and no greater than 6 mm.

19. An implantable bone plate comprising:
(a) a solid, elongated rod, void of any holes throughout its length, said rod including a bottom bearing surface; and
(b) a plurality of integral tab members protruding laterally from said solid rod and having a bottom surface extending in substantially the same plane as the bearing surface of the rod, said tab members having an aperture therein for receiving a bone screw or the like, and wherein said tab members have a thickness less than the thickness of the rod, said tab members spaced apart from each other along the length of the rod, said rod having a constant, substantially circular cross-sectional configuration throughout its length, enabling the rod to be easily contoured to fit particular contours of the bone to which the plate is to be affixed.

20. An implantable bone plate comprising:
(a) a solid, elongated rod, said rod including a bottom bearing surface; and
(b) a plurality of integral tab members extending laterally from said solid rod and having a bottom surface extending in substantially the same plane as the bearing surface of the rod, said tab members having an aperture therein for receiving a bone screw or the like, and wherein said tab members have a thickness less than the thickness of the rod.

21. An implantable bone plate as described in claim 20 wherein said rod is at least one and a half times greater in thickness than the tab members.

22. An implantable bone plate as described in claim 20 wherein said rod is at least three times greater in thickness than the tab members.

23. An implantable bone plate as described in claim 20 wherein the surface of said tabs engagable with the bone surface are planar and extend tangentially from the outer surface of the rod.

* * * * *